US00PP28757P3

(12) United States Plant Patent
Buechel

(10) Patent No.: US PP28,757 P3
(45) Date of Patent: Dec. 12, 2017

(54) ***HYDRANGEA* PLANT NAMED 'MCKAY'**

(50) Latin Name: *Hydrangea macrophylla*
Varietal Denomination: McKay

(71) Applicant: The CONARD-PYLE COMPANY, West Grove, PA (US)

(72) Inventor: Thomas J. Buechel, Lake Mills, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 14/757,788

(22) Filed: Dec. 29, 2015

(65) Prior Publication Data

US 2017/0188496 P1 Jun. 29, 2017

(51) Int. Cl.
*A01H 5/00* (2006.01)

(52) U.S. Cl.
USPC ..... Plt./250

(58) Field of Classification Search
USPC ..... Plt./250
See application file for complete search history.

(56) References Cited

U.S. PATENT DOCUMENTS

PP20,176 P3 * 7/2009 Dirr ..... Plt./250

* cited by examiner

*Primary Examiner* — Susan McCormick Ewoldt
(74) *Attorney, Agent, or Firm* — Buchanan Ingersoll & Rooney PC

(57) ABSTRACT

A new and cultivar of *Hydrangea macrophylla* was created by open pollination followed by selection. A compact rounded growth habit is displayed. Attractive deep rose blossoms are formed in abundance that contrast nicely with textured dark green foliage. Resistance to powdery mildew has been displayed during observations to date. Superior winter hardiness to at least U.S.D.A. Hardiness Zone No. 5 has been experienced.

1 Drawing Sheet

Botanical/commercial classification: *Hydrangea macrophylla/Hydrangea* Plant cv. McKay.

SUMMARY OF THE INVENTION

The new *Hydrangea* cultivar was developed at Waterloo, Wis., U.S.A. through the open pollination of diverse *Hydrangea macrophylla* plants followed by selection. The diverse parents were derived from Europe and were unnamed and non-patented. Seeds resulting from such open pollination were sown in containers during 2006. The resulting plants which were physically and biologically different from each other and were grown outdoors in containers under conditions typical of the harsh winter environment of the area. During July 2009 selective study resulted in the identification of a single new plant of the present cultivar. The selection was made on the basis of superior hardiness, excellent vigor, the display of pleasing inflorescence coloration, and the resistance to powdery mildew. Had this new plant not been selected and preserved it would have been lost to mankind. The female parent (i.e., the seed parent) and the male parent (i.e., the pollen parent) were both unknown.

It was found that the new *Hydrangea* plant of the present invention:

(a) forms in abundance attractive deep rose-colored lacecaps inflorescences,
(b) exhibits a compact rounded growth habit,
(c) displays attractive textured dark green foliage,
(d) displays resistance to powdery mildew during observations to date, and
(e) displays superior winter hardiness to at least U.S.D.A. Hardiness Zone No. 5.

The winter hardiness and resistance to powdery mildew are considered to be particularly noteworthy. The deep rose blossoms contrast nicely with the dark green foliage coloration.

The new cultivar well meets the needs of the horticultural industry and can be grown to advantage where attractive ornamentation is to be provided.

The new variety can be readily distinguished from other known *hydrangea* cultivars. For instance, the new variety has larger and darker colored sterile inflorescences, and larger foliage than the 'PIIHM-1' variety U.S. Plant Pat. No. 20,176.

The new cultivar has been found to undergo asexual propagation through successive generations by the rooting of softwood cuttings at Waterloo, Wis., U.S.A., and at West Grove, Pa., U.S.A. The new cultivar reproduces well through the use of softwood cuttings. Such asexually propagation has shown that the characteristics of the new cultivar are stable and are strictly transmissible from one generation to another. Accordingly, the new cultivar undergoes asexual propagation in a true-to-type manner.

The new cultivar has been named 'McKay'.

BRIEF DESCRIPTION OF THE PHOTOGRAPH

The accompanying photograph shows as nearly true as it is reasonably possible to make the same in a color illustration of this character, a typical specimen of the new cultivar. A flowering plant of the new cultivar having an age of approximately one year while growing outdoors in a threegallon container at Waterloo, Wis., U.S.A. is shown from above. The attractive deep rose blossoms and dark green foliage are shown.

DETAILED BOTANICAL DESCRIPTION

The chart used in the identification of the colors is that of The Royal Horticultural Society (R.H.S. Colour Chart) of London, England (2001). The description is based on the observation of typical specimens of the new cultivar at an age of approximately one year while growing in a greenhouse in West Grove, Pa., U.S.A., in one gallon containers under conditions which closely approximate commercial production conditions. Measurements and numerical values represent averages of typical plants.

Botanical classification: *Hydrangea macrophylla.*

Parentage: Open pollinated selection from parents of unknown origin.

Propagation:

*Type*.—Softwood cuttings.

*Number of days to initiate roots*.—Approximately 14 days.

*Number of days to produce a rooted cutting*.—Approximately 42 days.

Plant:

*Growth habit and general appearance*.—Compact grower with a rounded habit.

*Height*.—In ground: commonly approach approximately 3 feet.

*Width*.—In ground: commonly approach approximately 3 feet.

Branches:

*Type*.—Freely branching.

*Strength*.—Moderately strong.

*Length*.—Approximately 15 cm on average.

*Diameter*.—Approximately 5 mm on average.

*Texture*.—Smooth.

*Color*.—Near Yellow-Green Group 146C.

Foliage:

*Leaf arrangement*.—Opposite.

*Leaf texture*.—Upper and lower surfaces: thick and leathery.

*Leaf venation*.—Pattern: parallel. Color (upper and lower): near Yellow-Green Group 145A.

*Leaf color*.—Upper surface: near Green Group 139A. Lower surface: near Green Group 137B.

*Leaf shape*.—Ovate. Apex: acuminate. Base: cuneate.

*Leaf margin*.—Crenate.

*Leaf length*.—Approximately 13 cm on average.

*Leaf width*.—Approximately 11 cm on average.

*Petiole*.—Length: approximately 2 cm on average. Diameter: approximately 5 mm on average. Texture: smooth, glabrous. Color: near Yellow-Green Group 145A.

Inflorescence:

*Number of fertile flowers*.—Commonly approximately 80 to 100.

*Shape*.—Lacecap.

*Length*.—Approximately 19 cm on average.

*Width*.—Approximately 12 cm on average.

*Buds*.—Length: approximately 4 mm on average. Width: approximately 4 mm on average. Depth: approximately 3 mm on average. Shape: round. Color: near Red-Purple Group 67A.

*Peduncle*.—Length: approximately 3 cm on average. Texture: finely pubescent. Color: near Red-Purple Group 67A.

*Sterile florets*.—Number of sepals: 4. Length: approximately 3 cm on average. Width: approximately 4.5 cm on average. Shape: ovoid. Apex: obtuse. Base: cuneate. Margin: entire. Texture: smooth. Color — upper surface: near Red-Purple Group 67A. Color — lower surface: near Red-Purple Group 66C.

*Petals* (*fertile flowers*).—Number: 5 petals per flower. Length: approximately 6 mm on average. Width: approximately 6 mm on average. Shape: ovate. Apex: acute. Base: rounded. Margin: entire. Texture: smooth with no pubescence. Color — upper surface: near Red-Purple Group 67A outlined with near White Group 155B. Color — lower surface: near Red-Purple Group 67A.

*Stamens*.—Number: 10.

*Anthers*.—Length: approximately 1 mm on average. Width: approximately 1 mm on average. Color: near White Group 155B.

*Filaments*.—Length: approximately 6 mm on average. Width: approximately 0.5 mm on average. Color: near White Group 155B.

*Pollen*.—Color: close to White Group 155B.

*Pistil*.—Type: superior. Length: approximately 3 mm on average. Width: approximately 1 mm on average.

*Stigma*.—Number: 3 or 4 per pistil. Shape: round. Color: close to White Group 155B.

*Style*.—Length: approximately 1 mm on average. Shape: tubular. Color: close to Red-Purple Group 65C.

*Fruit*.—Shape: ovoid. Length: approximately 5 mm on average. Width: approximately 3 mm on average. Color (at maturity): close to Brown Group 200C.

*Seed*.—Not observed to date.

Development:

*Inflorescence duration*.—The inflorescence is effective for about 8 weeks.

*Inflorescence bloom period*.—Early summer to first frost in fall.

*Tolerance to disease*.—Resistance to stresses, pathogens, and pests.

The new 'McKay' cultivar has not been observed under all possible environmental conditions to date. Accordingly, it is possible that the phenotypic expression may vary somewhat by changes in light intensity and duration, cultural practices, and other environmental conditions.

I claim:

1. A new and distinct *Hydrangea* plant characterized by the following combination of characteristics:

(a) forms in abundance attractive deep rose-colored lacecap inflorescences, (b) exhibits a compact rounded growth habit, (c) displays attractive textured dark green foliage, (d) displays resistance to powdery mildew during observations to date, and (e) displays superior winter hardiness to at least U.S.D.A. Hardiness Zone No. 5;

substantially as illustrated and described.

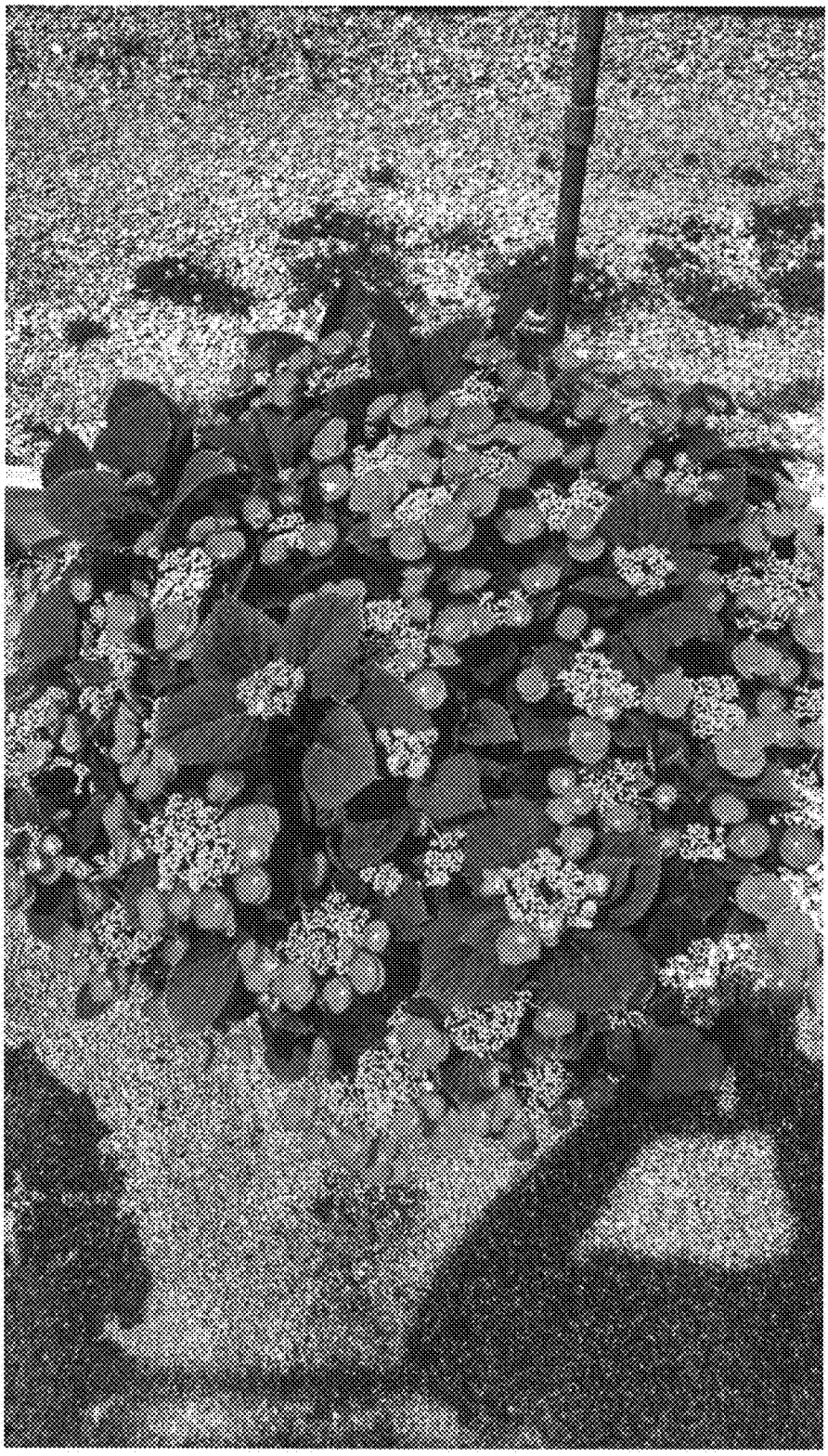

* * * * *